United States Patent
Safai (10) Patent No.: US 9,494,561 B1
(45) Date of Patent: Nov. 15, 2016

(54) QUANTUM MICROPHONE ARRAY FOR TESTING THE STRUCTURAL INTEGRITY OF AN OBJECT

(71) Applicant: The Boeing Company, Chicago, IL (US)

(72) Inventor: Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 386 days.

(21) Appl. No.: 14/024,053

(22) Filed: Sep. 11, 2013

(51) Int. Cl.
*G01N 29/34* (2006.01)
*G01N 29/44* (2006.01)
*G01N 29/04* (2006.01)

(52) U.S. Cl.
CPC ............ *G01N 29/34* (2013.01); *G01N 29/045* (2013.01); *G01N 29/4445* (2013.01)

(58) Field of Classification Search
CPC ............... G01N 29/34; G01N 29/045; G01N 29/2418; G01N 29/2431; G01N 29/4445; G01N 29/46
USPC ........................... 73/579, 583, 584, 588, 587
See application file for complete search history.

(56) References Cited

U.S. PATENT DOCUMENTS

| | | | | |
|---|---|---|---|---|
| 7,647,206 B2* | 1/2010 | Ford | ................... | G01N 29/4409 702/183 |
| 2008/0138797 A1* | 6/2008 | Hunt | ........................ | B82Y 5/00 435/6.16 |
| 2012/0055243 A1* | 3/2012 | DiFoggio | ................. | G01V 1/52 73/152.58 |
| 2013/0061678 A1* | 3/2013 | Yamamoto | ........... | A61B 5/0095 73/602 |

OTHER PUBLICATIONS

Ekinci, K. et al. "Electromechanical Transducers at the Nanoscale: Actuation and Sensing of Motion in Nanoelectromechanical Systems (NEMS)", Small, (2005), pp. 786-797, vol. 1, Issue No. 8-9.*
Knobel, R. et al., "Piezoelectric displacement sensing with a single-electron transistor", Applied Physics Letters, Sep. 16, 2002, pp. 2258-2260, vol. 81, Issue No. 12.*
Pikarski, B. et al.. "Surface micromachined piezoelectric resonant beam filters", Sensors and Actuators A. (2001), pp. 313-320, vol. 91.*
Physics News, Quantum Microphone Captures Extremely Weak Sound, http://www.physnews.com/physics-news/cluster215139117, Retrieved Jun. 4, 2013.
Quantum Microphone Captures Extremely Weak Sound, http://www.sciencedaily.com/releases/2012/02/120227093954.htm, Feb. 27, 2012.
David Castelvecchi, Macro-Weirdness: "Quantum Microphone" Puts Naked-Eye Object in 2 Places at Once, Scientific American, http://www.scientificamerican.com/article.cfm?id=quantum-microphone, Mar. 28, 2010.

* cited by examiner

*Primary Examiner* — Laura Martin
*Assistant Examiner* — Rose M Miller
(74) *Attorney, Agent, or Firm* — Kunzler Law Group, PC (57) ABSTRACT

The present disclosure relates to a system for testing a structure of an object. According to one embodiment, the system includes a vibration initiator that imparts an acoustic shockwave to an object. The system also includes an acoustic detector array that senses the acoustic shockwave as it propagates through the object, in which the acoustic detector array comprises a plurality of quantum microphones. The system further includes a reporting unit that receives sensed acoustic shockwave data from the acoustic detector array and produces a structural integrity report.

20 Claims, 7 Drawing Sheets

QUANTUM MICROPHONE ARRAY FOR TESTING THE STRUCTURAL INTEGRITY OF AN OBJECT

FIELD

This disclosure relates to testing the structural integrity of an object and more particularly relates to a system that uses a plurality of quantum microphones to detect the presence of cracks and other structural anomalies in an object.

BACKGROUND

There are many systems and methods for testing the strength of a material. Generally, the strength of a material is determined by its ability to withstand an applied load. Accordingly, many testing procedures involve applying an increasing load on a material and observing when the material elastically deforms (i.e., the range in which the material does not suffer any permanent damage or distortion), when the material plastically deforms (i.e., the range in which the material still is capable of sustaining a load but permanent damage and distortion have occurred, resulting in permanent structural defects), and when the material reaches its failure point. These testing procedures are often termed 'destructive' because the material being tested is often destroyed or at least permanently deformed to the point that it is no longer useable for its intended application.

Additionally, conventional strength tests are generally performed ex situ and usually include applying shear, compression, and/or tensile type forces to a test material. For example, when conventionally testing a metallic or a composite component of an aircraft, the component is often removed from its position in the frame (i.e., the frame is disassembled to a certain degree) or a mock component is tested instead of the actual component and the results of the test component are deemed representative of the actual component. Continuing the example of components in aircrafts, many governmental airline agencies, such as the Federal Aviation Agency (FAA) in the United States, specify periodic maintenance checks to be performed to ensure the safe operation of all the aircrafts within their jurisdictions. For example, 'C-checks' and 'D-checks' are maintenance checks that are specified to be performed by the FAA every few years on airplanes in the United States and such checks often involve component inspection. Because conventional strength testing systems and methods are performed ex situ, these checks often involve substantial cost and expense as the testers may disassemble large portions of the aircraft. In other words, conventional testing systems and procedures are not well suited for testing the strength of components in situ.

Ultrasonic testing, however, overcomes some of these shortcomings because it is a non-destructive procedure and it can be implemented in-situ. Ultrasonic testing involves using transducers to impart a vibration into a material and measure the resultant feedback vibration. Depending on the characteristics of the feedback vibration, a user can identify locations in the material where the crystal lattice has abnormalities or defects. The oscillating pressure wave imparted to the material is deemed ultrasonic when the frequency of the wave is higher than the upper limit of the human hearing range. Thus, conventional ultrasonic systems generally involve waves with a frequency in the range of between about 20 kHz (20,000 Hz) and 10 MHz (10,000,000 Hz). Comparatively lower frequency sound waves can penetrate comparatively deeper into a material than higher frequency sound waves, but the higher frequency sound waves are able to detect smaller abnormalities and defects.

However, conventional ultrasonic inspection systems are unable to detect some micro and nano sized cracks and are also unable to detect some sub-surface closed cracks. This is due, in part, because the sensors and transducers that have been conventionally used in ultrasonic inspection systems are incapable of sensing the propagation of super high frequency acoustic vibration waves (i.e., waves with a frequency higher than about 10 MHz) through a test material. Additionally, conventional ultrasonic inspection systems are unable to adequately inspect the structural integrity of thin films and coatings. While there are sensors that are capable of detecting such high frequency vibrations, conventional ultrasound inspection systems have not used such sensors to produce 2-dimensional scans of a material. In other words, the sensors that have been conventionally used to detect such high frequency vibrations are typically large, in comparison to the cracks that they are supposed to detect, and have not been used in conjunction with other sensors. Thus some conventional ultrasound inspection systems are used as point-by-point inspection tools and, as mentioned, have not been used to create a 2-dimensional structural analysis of a material.

SUMMARY

The subject matter of the present disclosure has been developed in response to the present state of the art, and in particular, in response to the limitations of conventional ultrasonic testing and inspection systems. Specifically, conventional ultrasound testing methods and systems do not allow for objects to be inspected for the presence of micro sized (or smaller) cracks, especially in thin materials where the cracks are closed or are sub-surface. Accordingly, the subject matter of the present disclosure has been developed to provide an apparatus, system, and method for using high frequency ultrasonic waves to inspect materials that overcome at least some of the above-discussed shortcomings of the prior art.

The present disclosure relates to a system for testing a structure of an object, which in some implementations can include detecting structural anomalies in a solid object. According to one embodiment, the system includes a vibration initiator that imparts an acoustic shockwave to an object. The system also includes an acoustic detector array that senses the acoustic shockwave as it propagates through the object, in which the acoustic detector array comprises a plurality of quantum microphones. The system further includes a reporting unit that receives sensed acoustic shockwave data from the acoustic detector array and produces a structural integrity report. According to one implementation, timing of imparting the acoustic shockwave to the object is correlated with timing of detecting the acoustic shockwave.

In one embodiment, the vibration initiator is a laser. In another embodiment, the vibration initiator is a diamond particle pinging subsystem. The frequency of the vibration shockwave may be greater than 10 MHz in certain implementations. Further, in one embodiment the number of quantum microphones on the acoustic detector array is greater than 100. The quantum microphones may include a single-electron transistor. In one implementation, the acoustic detector array is flexible. In one embodiment, the structural integrity report comprises a 2-dimensional image of the structural anomalies of the object. Also, the vibration initiator and the acoustic detector array may be co-movably fixed together.

The present disclosure also relates to a controller apparatus. The controller apparatus, according to one embodiment, includes an initiation module that sends an acoustic shockwave command to a vibration initiator. The apparatus also includes a detector module that sends sensing commands to a plurality of quantum microphones on an acoustic detector array, receives sensed acoustic shockwave data from the plurality of quantum microphones on the acoustic detector array, and produces an acoustic shockwave report based on the sensed acoustic shockwave data. The controller apparatus may also include a data module that receives the acoustic shockwave report from the detector module and produces a structural integrity report.

According to one embodiment, the initiation module sends a timing correlation command to the detector module, wherein the detector module sends sensing commands to the plurality of quantum microphones on the acoustic detector array according to the timing correlation command. In one embodiment, the vibration initiator is a laser. In another embodiment, the vibration initiator is a diamond particle pinging subsystem. The frequency of the vibration shockwave may be greater than 10 MHz in certain implementations. Further, in one embodiment the number of quantum microphones on the acoustic detector array is greater than 100. The quantum microphones may each comprise a single-electron transistor. In one implementation, the acoustic detector array is flexible. In one embodiment, the structural integrity report comprises a 2-dimensional image of the structural anomalies of the object.

Still further, the present disclosure also relates to a method for testing a structure of an object, which may include detecting cracks and structural anomalies in the object according to some implementations. According to one embodiment, the method includes imparting an acoustic shockwave to the object. The method further includes detecting the acoustic shockwave as it propagates through the object, wherein a plurality of quantum microphones may be used to sense the acoustic shockwave. Further, the method includes receiving sensed acoustic shockwave data from the quantum microphones and producing a structural integrity report based on the sensed acoustic shockwave data. The timing of imparting the acoustic shockwave to the object may be correlated with the timing of detecting the acoustic shockwave and the shockwave imparted to the object may have a frequency greater than 10 MHz, in one embodiment.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Figure 1:
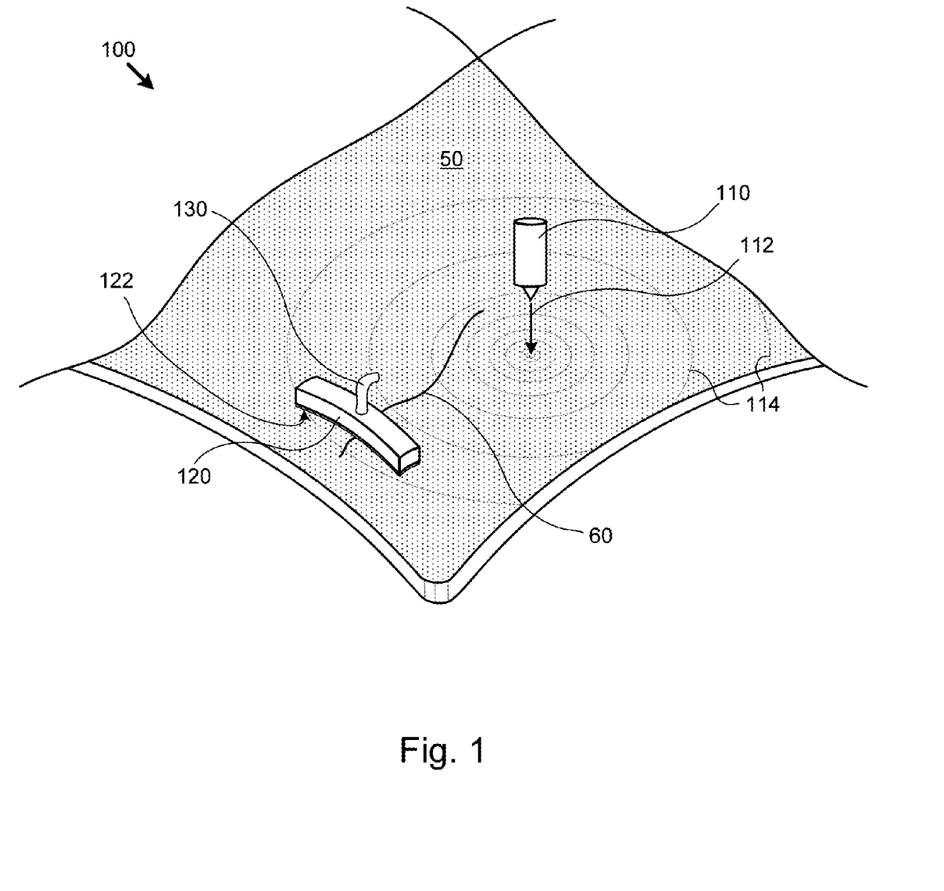
FIG. 1 depicts a system for detecting cracks and structural anomalies in an object, wherein the system includes a vibration initiator, an acoustic detector array, and a reporting unit, according to one embodiment.

FIG. 1 depicts a system 100 for detecting cracks 60 and structural anomalies in an object 50, wherein the system includes a vibration initiator 110, an acoustic detector array 120, and a reporting unit 130, according to one embodiment. As described briefly above, the system of the present disclosure provides a method for a user/inspector to test for the presence of micro and nano sized cracks 60 in the crystal lattice structure of an object 50. More specifically, in some embodiments the system disclosed also provides a way for a user/inspector to test for the presence of closed, subsurface cracks. Throughout the present disclosure, the term crack 60 will be used to refer to any type of structural anomaly or crystal lattice defect. For example, the term crack 60 may be used to refer to any point, line, or planar defect present in a material.

Also, throughout the present disclosure, the use of the term object 50 will refer to any solid component or material to be tested that has a substantially crystalline morphology. For example, the object 50 to be tested may be a metallic component in the frame of an aircraft. In another embodiment, the object 50 may be a composite component in medical device or a ceramic element of a research apparatus. The tested material may also include ceramics, fiber embedded ceramics, and metal matrix ceramics, among other materials. As mentioned above, the object 50 may actually be a coating or a thin film applied over the top of another material/component. In another embodiment, the object 50 to be tested may be substantially thick and only a portion of the object 50 near the surface will be tested. The depth of the inspection depends on the frequency of the vibrations imparted to the object 50. The higher the frequency, the shallower the waves will travel and thus the inspection depth of the object 50 will decrease.

In order to create such a high frequency vibration shockwave 114 in the object, the vibration initiator 110 may pulse the surface of the object 50 with energy. The acoustic shockwave 114 depicted in FIG. 1 is shown at progressive stages of propagation. In other words, the vibration initiator 110, in one embodiment, initiates a single wave that propagates outward. To show the propagation of the acoustic shockwave 114, concentric circles are shown in FIG. 1 depicting the movement of the wave (i.e., a single wave) through the object 50. There are various methods for imparting a high frequency acoustic shockwave 114 into an object 50. For example, the vibration initiator 110 may comprise a laser that stimulates high frequency thermal vibration movement in the object 50. The pulse 112 from a laser introduces heat into the crystalline structure of the object 50, which in turn instigates a high frequency crystal lattice vibration. In another embodiment, hitting the surface of the object 50 with a small device, such as a diamond particle 112, may initiate the propagation of a high frequency acoustic shockwave 114 through the object 50 or at least along the surface of the object 50.

Throughout the present disclosure, the term 'excitation medium' 112 will refer to the energy or material that is used to pulse or ping the surface of the object 50. It is contemplated that other devices or sub-systems that can produce high frequency lattice vibrations, as recognized by those of ordinary skill in the art, fall within the scope of the present disclosure. For example, the excitation medium 112 may include a single pulse from an electric field, a pulse of electric current, a pulse from a magnetic field, and induction current loading. Additionally, the excitation medium 112 may be modulated using the techniques disclosed above in order to develop a signal average or to improve the signal-to-noise ratio. In another embodiment, the surface of the acoustic shockwave 114 can be imparted to the object 50 through the use of residual stress from mechanical loading (e.g., compression, shear, and tensile loading) and/or thermal loading using a thermal blanket (e.g., temperature cycling subsystems).

Also, as mentioned briefly above, it is contemplated that the vibration initiator 110 will produce an acoustic shockwave 114 with a wave frequency greater than 10 MHz. According to one embodiment, the vibration initiator 110 will emit an excitation medium 112 at a single point on the surface of the object 50. The excitation medium 112 may only be a short pulse (heat or electrical energy delivered to the object) or a rapid ping (mechanical contact with the object) that initiates an acoustic shockwave 114 that ripples outwards, like the ripple-effect on the surface of a liquid, propagating outwards from the initial excitation point. The actuation of the excitation medium 112 by the vibration initiator 110 may be synchronized and correlated with the actuation of the acoustic detector array 120. Details relating to the timing synchronization/correlation between the vibration initiator 110 and the acoustic detector array 120 are included below with reference to FIG. 4B.

Figure 2A:
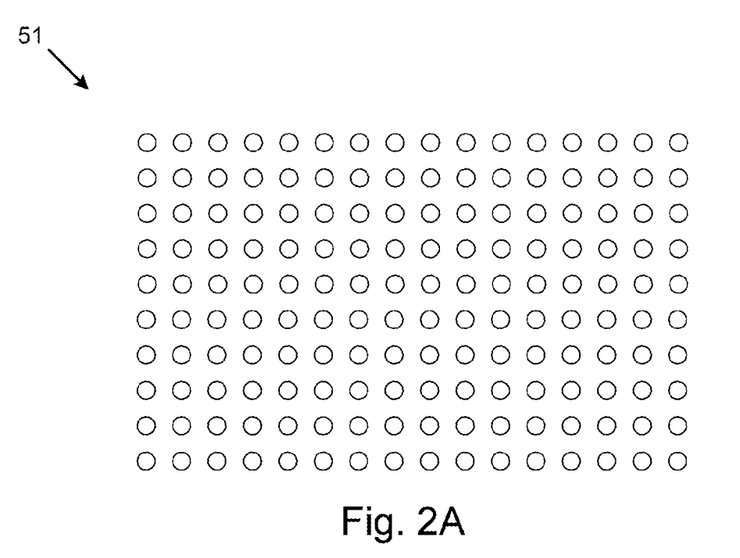
FIG. 2A depicts the crystal lattice of an object that is not experiencing crystal lattice structural vibration, according to one embodiment.

FIG. 2A depicts the crystal lattice of an object 50 that is not experiencing crystal lattice structural vibration, according to one embodiment. FIG. 2A includes a simplified depiction of a single plane of atoms in a crystal lattice structure. The present depiction of the crystal lattice is not intended to limit the scope of the present disclosure. Rather, FIGS. 2A and 2B have been included to show how the acoustic shockwave 114 propagates through an object 50. In other words, the present disclosure is not limited to objects 50 with a specific crystal lattice structure as depicted.

Figure 2B:
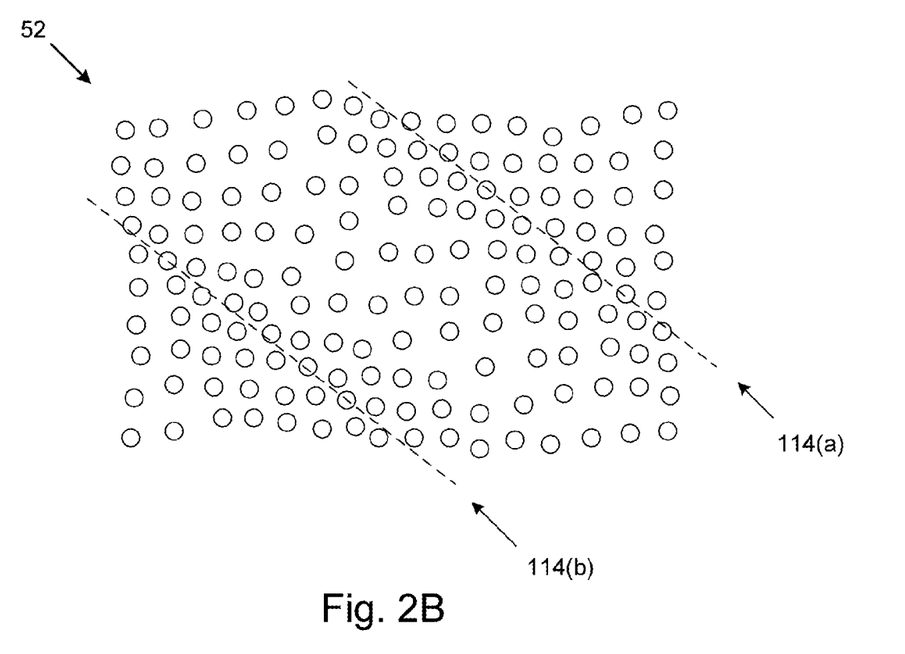
FIG. 2B depicts the crystal lattice of an object that is experiencing crystal lattice structural vibration, according to one embodiment.

FIG. 2B depicts the crystal lattice from FIG. 2A but shows the displacement of atoms when the object 50 is experiencing crystal lattice structural vibration, according to one embodiment. Although the displacement of the atoms is greatly exaggerated, FIG. 2B shows a single acoustic shockwave as it propagates through the crystal lattice of an object 50. As described above, it is contemplated that a single acoustic shockwave 114 will be initiated to propagate across the object 50. FIG. 2B shows an acoustic shockwave at a first point in time 114(*a*) and the same acoustic shockwave at a second point in time 114(*b*) as it moves through the object. The vibration or oscillation of atoms in a solid crystal lattice structure at a single frequency is known as a phonon. A phonon is a quantum mechanical description of a collective excitation of atoms; a quantum of sound energy. Since a quantum is the minimum amount of something in an interaction, a phonon, in terms of the present disclosure, is the smallest discrete increment of sound emanating from the lattice vibration of the acoustic shockwave 114. Thus, the acoustic shockwave 114 of the present disclosure has a high frequency that is high enough and initiated by pulse/ping with an intensity (e.g., energy) that is low enough that the vibration of the crystal lattice structure produces sound at the quantum level.

Figure 3:
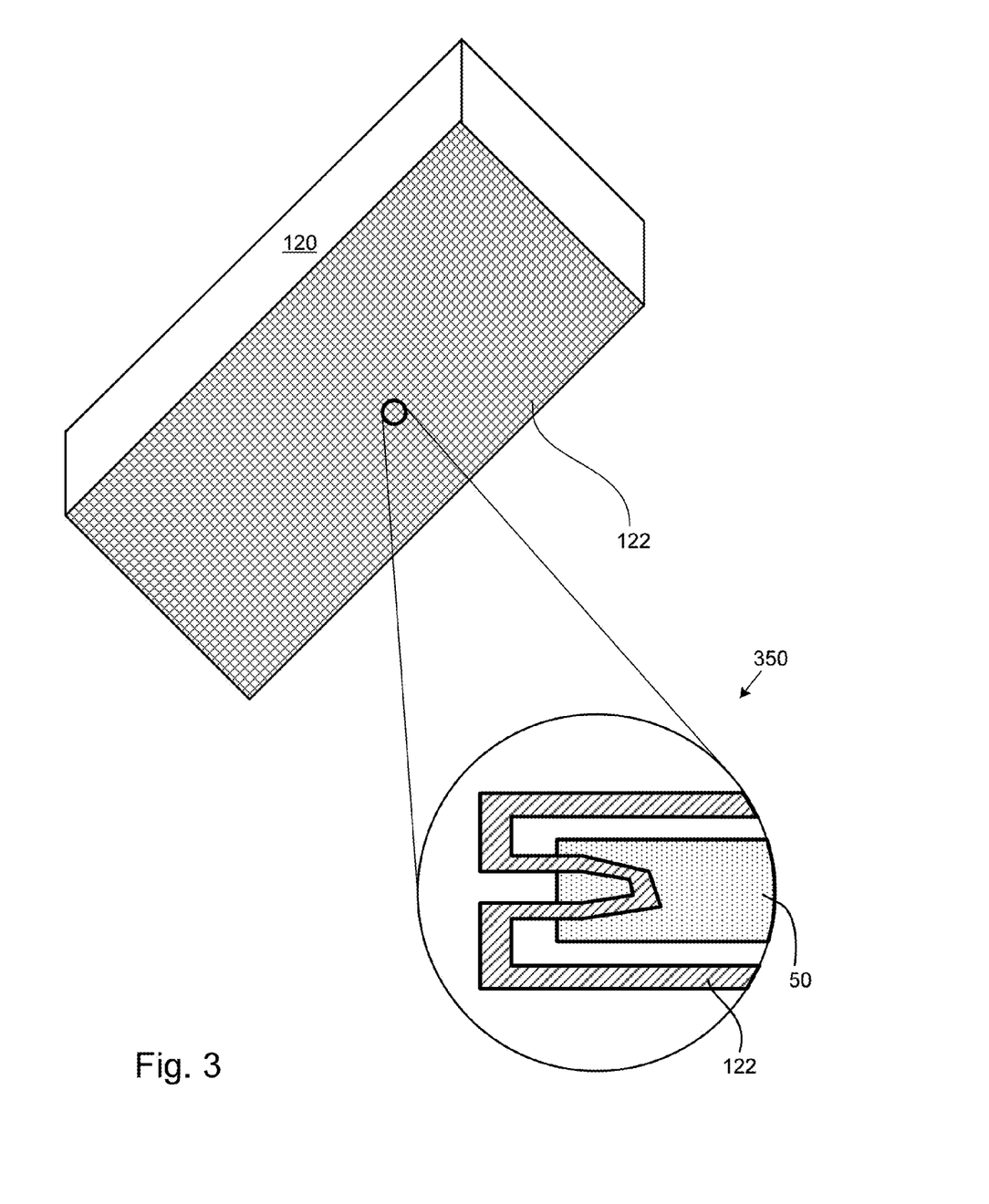
FIG. 3 depicts a plurality of quantum microphones on an acoustic detector array and depicts a magnified view of a single quantum microphone, according to one embodiment.

FIG. 3 depicts a plurality of quantum microphones 122 on an acoustic detector array 120 and depicts a magnified view 350 of a single quantum microphone 122, according to one embodiment. As described above, the acoustic detector array 120 has an arrangement of many individual quantum microphones 122 that can each independently sense acoustic vibration. The detector array 120 is positioned above the area of the object 50 to be inspected, in close proximity to the surface. In some embodiments, the detector array 120 is in contact with (e.g., resting on) on the surface of the object 50. With the individual quantum microphones 122 in an array and each detecting the feedback vibration at a point, the resultant structural integrity report is a 2-dimensional scan of the crystalline structure of the object 50. The detector array 120, although depicted as having a rectangular shape, may have a variety of shapes and/or configurations. For example, the acoustic detector array 120 may be circular, triangular, square, or otherwise configured. In one embodiment, the detector array 120 may be configured according to the specifics of a given application. For example, the detector array 120 may be an elongated rectangle extending across the width of an object 50.

The detector array 120 may be systematically moved across the object 50 (e.g., along a length or width), measuring and sensing the vibration feedback from the acoustic shockwave. In such an example, the entire surface area of the object 50 may be inspected by moving the detector array 120 across the area of the object 50. The size (i.e., the effective cross-sectional area) of the detector array 120 may depend on the specifics of a given application. In one embodiment, the cross-sectional area of the detector array 120 is about 1 square inch. In another embodiment, the cross-sectional area of the detector array 120 may be about 5 square inches. Also, the detector array 120 may be flexible in order to conform with and contour the shape of an object 50. The size of the detector array 120 may depend on the size and number of quantum microphones 122.

A quantum microphone 122 is a device that is capable of sensing acoustic vibration at the quantum level. In one embodiment, a single electron transistor functions as a quantum microphone 122. Most crystalline structures, when deformed, experience a piezoelectric-like effect when the atoms vibrate. The vibration of the atoms' electrons causes a small change in the electrical polarity of the atoms. This change in polarity can be detected by a single electron transistor. Accordingly, the intensity of the electrical signal that is detected by the single electron transistor is representative of the structure of the crystalline lattice. It is contemplated that other devices that are capable of detecting such small acoustic vibrations fall within the scope of the present disclosure and may be used as quantum microphones 122. In one embodiment, as depicted in the magnified cross-sectional view 350 of FIG. 3, a single quantum microphone 122 may have a piezoelectric resonator material interposed between two layers of aluminum. The layers of aluminum function as electrodes through which the piezoelectric effect is communicated to a controller for analysis. The rectangular object 50 depicted in the magnified view 350 generally embodies the material to be tested and is not an actual representation of the material to be tested.

Because the quantum microphones 122 are detecting diminutive lattice vibrations, it is anticipated that the testing site will be substantially quiet and will not have any disturbances that might disturb the accuracy of the sensed shockwave data detected by the quantum microphones 122. The number and the size of the quantum microphones 122 on the detector array 120 are proportional to the resolution of the scan. The size and quantity of the detectors determines the resolution of the resultant report/image. As the size of the quantum microphones 122 decrease, the resultant structural integrity report will be sharper (the structural integrity report will be described in greater detail below with reference to FIG. 5). In one embodiment, the detector array 120 may have hundreds of quantum microphones 122. In another embodiment, the detector array 120 may have thousands of quantum microphones 122.

Figure 4A:
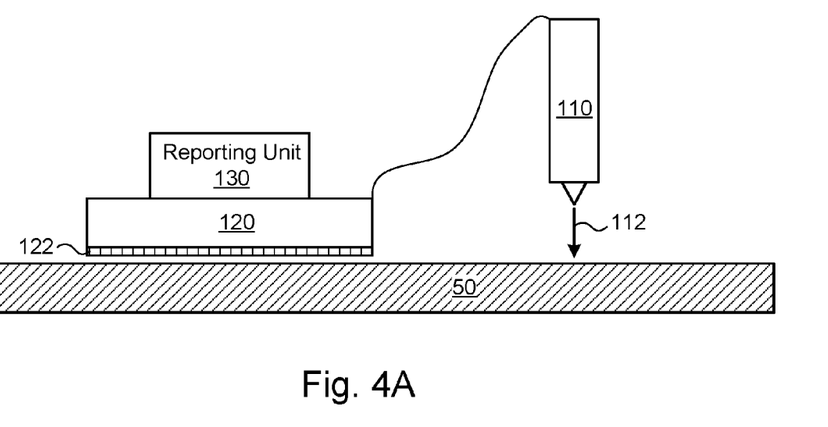
FIG. 4A depicts one embodiment of a system for detecting cracks and structural anomalies in an object where the vibration initiator is separated from the conjoined acoustic detector array and reporting unit.

FIG. 4A depicts one embodiment of a system for detecting cracks and structural anomalies in an object 50 where the vibration initiator 110 is separated from the acoustic detector array 120 and the reporting unit 130, which are co-movably fixed together. In the depicted embodiment, the vibration initiator 110 is displaced a distance from the detector array 120. In such a configuration, the intensity of the acoustic shockwave may have dissipated by the time it reaches the detector array 120. In certain situations, the dissipation of the shockwave may be beneficial because, without the dissipation, the intensity of the shockwave may exceed the sensitivity limits of the quantum microphones 122. In another embodiment shown in FIG. 4B, the vibration initiator 110 may be configured to attach, somewhat permanently to the object 50 during the inspection procedure. In such a configuration, the detector array 120 may still be able to move across the object 50 to get a scan of the entire surface, but the vibration initiator 110 will not need to be separately moved or repositioned. In another embodiment, the opposite configuration may be employed where the detector array 120 is temporarily fixed in place and the vibration initiator 110 is moved to different positions. Such a configuration may be used to calibrate the system.

The reporting unit 130 receives a shockwave report based on the sensed shockwave data from the detector array 120 and generates a structural integrity report. Additionally, the reporting unit 130 may record and store sensed shockwave data to be analyzed at a different time. The reporting unit 130, as depicted in FIG. 4A, may be coupled to the detector array 120. However, in other embodiments, the reporting unit 130 may be remotely located, as in FIG. 4B, and the detector array 120 may transmit data to the reporting unit 130 via a hard-line connection or through other wireless communication networks. Additional details relating to the reporting unit 130 are included below with reference to FIG. 6.

Figure 4B:
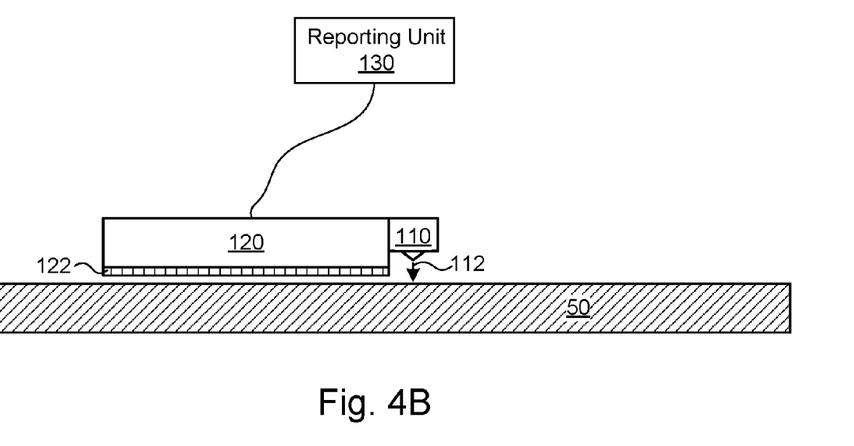
FIG. 4B depicts another embodiment of a system for detecting cracks and structural anomalies in an object where the vibration initiator and the acoustic detector array are conjoined and are separated from the reporting unit.

FIG. 4B depicts another embodiment of a system for detecting cracks and structural anomalies in an object 50 where the vibration initiator 110 and the acoustic detector array 120 are co-movably fixed together and are separated from the reporting unit 130. In the depicted embodiment, the vibration initiator 110 and the acoustic detector array 120 are both mounted together on a single probe. In such a configuration, the distance between the vibration initiator 110 and the detector array 120 is fixed, which may facilitate the inspection process because the distance between the shockwave initiation point and the quantum microphones 122 does not need to be determined each time the detector array changes 120 position.

Although described in greater detail below with reference to FIG. 6, in certain configurations it may be beneficial for the vibration initiator 110 and the detector array 120 to be synchronized or at least have a known distance and timing correlation between in order to accurately detect and report the shockwave data. In other words, the timing of the ping/pulse of the excitation medium 112 and the timing of the 'detecting' may be correlated to improve and ensure an accurate inspection. It is also contemplated that the system may be manually adjusted or automatically adjusted. However, due to the extremely sensitive nature of the measurements and the quantum nature of the vibrations that are being detected, it is anticipated that automatic configurations will be more accurate and will produce better results. In other words, the movement and placement of the various components may be controlled by a robotic subsystem.

Figure 5:
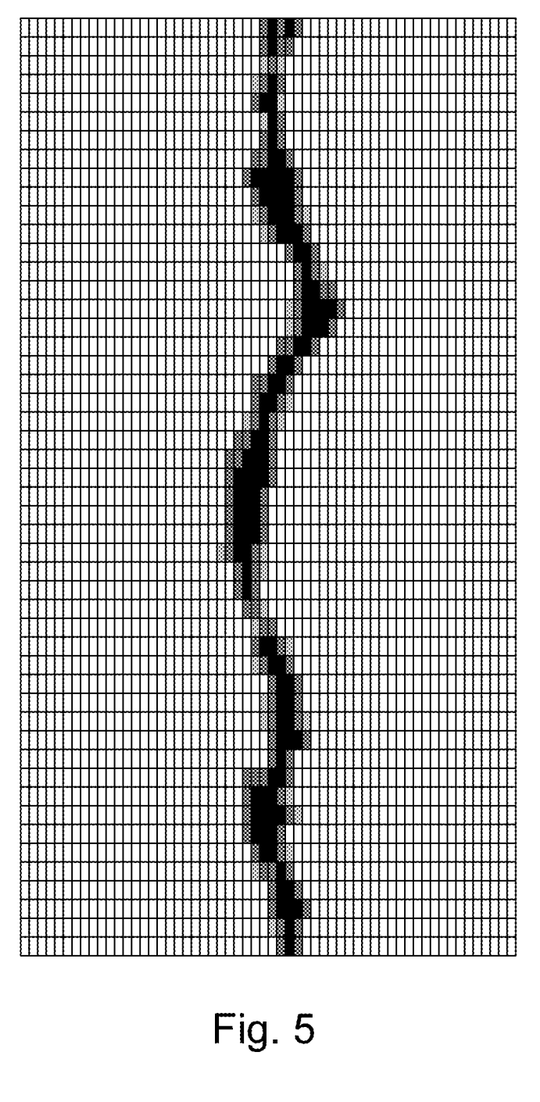
FIG. 5 depicts one embodiment of a structural integrity report that shows a crack in the object.

FIG. 5 depicts one embodiment of a structural integrity report that shows a crack in the object. As described above, the reporting unit 130 generates a structural integrity report based on the sensed acoustic shockwave data from the detector array 120. In one embodiment, as depicted, the structural integrity report includes an 'image' of the sensed shockwave data. In the depicted image, each rectangular pixel corresponds to a single quantum microphone 122. The color of the pixel represents a certain quantized data value. For example, the darker pixels may correspond with locations on the object where the vibration feedback wave that was detected by the quantum microphones 122 had a certain value. In one embodiment, the quantized intensity of the vibration measured by the quantum microphones 122 may be comparatively lower when crystalline defects or anomalies are present. Thus, in the depicted embodiment, the darker pixels may correspond with the positions on the object 50 where cracks are located. Once again, the resolution of the image depends on the number and size of the quantum microphones 122. In other embodiments, the structural integrity report may comprise a chart, table, graph, listing, or other form of information. Also, the measured value from the quantum microphones 122 may comprise intensity of vibration, orientation of vibration, or frequency of vibration, etc.

Figure 6:
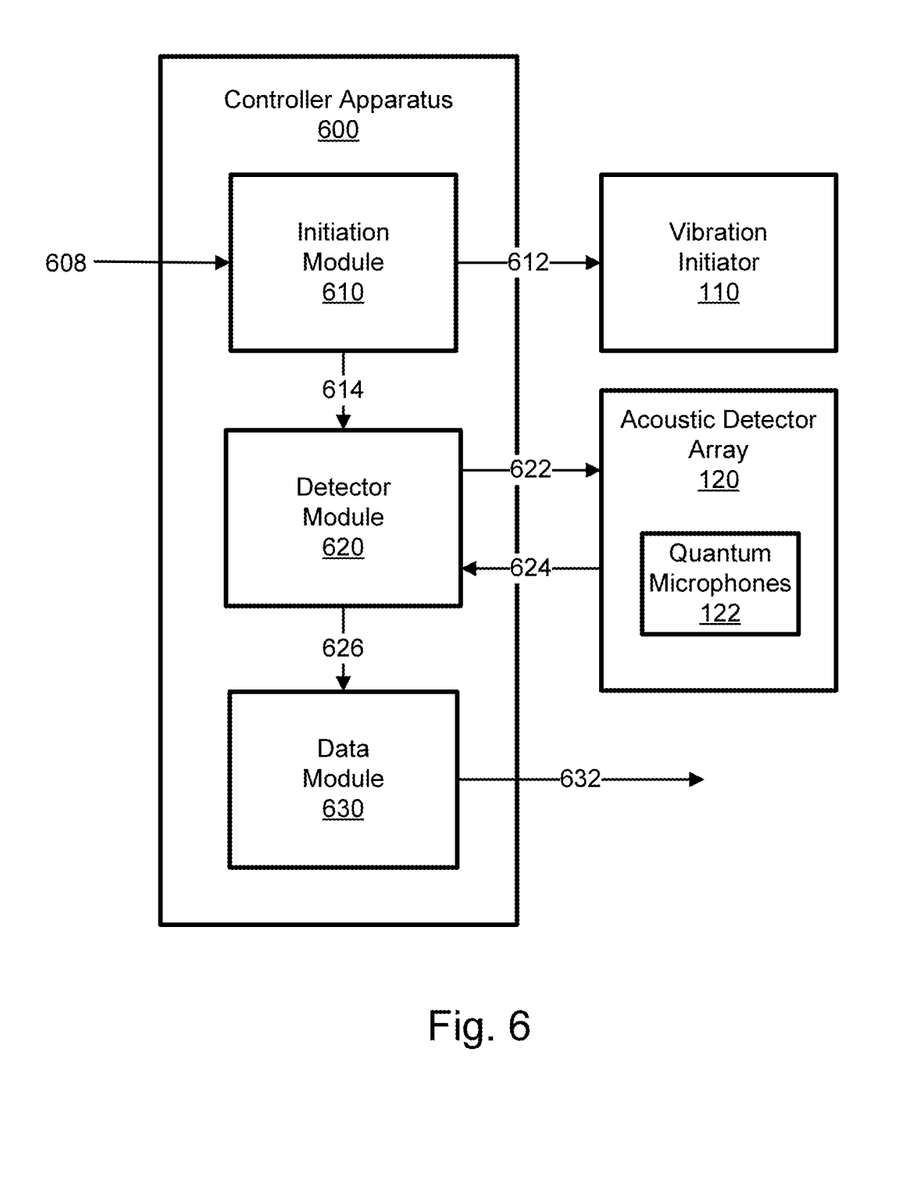
FIG. 6 depicts a controller apparatus for detecting cracks and structural anomalies, the controller apparatus including an initiation module, a detector module, and a data module, according to one embodiment.

FIG. 6 depicts a controller apparatus 600 for detecting cracks and structural anomalies, wherein the controller apparatus 600 includes an initiation module 610, a detector module 620, and a data module 630, according to one embodiment. The various modules of the controller apparatus may be stored and operated from separate components of the system (e.g., the initiation module may be housed in the vibration initiator) or the modules may be stored and operated from a central processing unit. The initiation module 610 controls the commencement of an inspection procedure. The activation/actuation of the initiation module 610 may be triggered by a user request 608 or some other commencement command 608 (e.g., may be automatically set based upon a timing variable). The initiation module 610 sends an acoustic shockwave command 612 to the vibration initiator 110. The acoustic shockwave command 612 may include the intensity, the frequency of vibration, the duration of the ping/pulse, and the position of the ping/pulse, among other variables. The initiation module 110 also, in certain embodiments, may send a timing correlation command 614 to the detector module 620. The timing correlation command 614, as briefly described above, may include synchronization instructions for the detector module 620 to incorporate into its sensing commands 622.

The detector module 620 controls the quantum microphones 122 by sending sensing commands 622 to the acoustic detector array 120. The sensing commands 622 may include the timing of when to activate the quantum microphones 122, the activation duration of the quantum microphones 122, and the location/position of the detector array 120, among others. The timing correlation command 614 received by the detector module 620 may be incorporated into the sensing commands 622 in order to synchronize the initiation of the shockwave with the detection of the shockwave vibrations. In one embodiment, depending on the intensity and frequency of the acoustic shockwave and the distance between the vibration initiator 110 and the detector array 120, the timing correlation command 614 may include a time delay, wherein the quantum microphones 122 are to only be activated at a certain time when the acoustic shockwave has propagated to the proper position. In another embodiment, instead of activating the quantum microphones at a certain time, the quantum microphones may be actively recording/inspecting but the timing correlation command 614 may include instructions pertaining to which data points are to be ignored and which data points are to be recorded, stored, and/or transmitted to the reporting module 630.

After the detection module sends out the sensing commands 622, the data collected by the acoustic detector array 120 is sent back to the detector module 620 as sensed acoustic shockwave data 624. The shockwave data 624 may include intensity of the vibration, orientation of the vibration, frequency of the vibration, and duration of the vibration, among other variables. Once the detector module 620 receives the shockwave data 624, the detector module sends that data 624 to the data module as an acoustic shockwave report 626. The shockwave report 626 is received and analyzed by the data module 630 and the data module 630 generates a structural integrity report 632 based on the shockwave report 626. In one embodiment, as depicted above in FIG. 5, the structural integrity report 632 may include an 'image' of the sensed shockwave data 624. In the image of FIG. 5, each rectangular pixel corresponds to a single quantum microphone 122. The color of the pixel represents a certain quantized data value. For example, the darker pixels may correspond with locations on the object where the vibration feedback wave that was detected by the quantum microphones 122 has a certain value. In one embodiment, the quantized intensity of the vibration measured by the quantum microphones 122 may be comparatively lower when crystalline defects or anomalies are present. Thus, in the depicted embodiment, the darker pixels may correspond with the positions on the object 50 where cracks are located. Once again, the resolution of the image depends on the number and size of the quantum microphones 122. In other embodiments, the structural integrity report 632 may comprise a chart, table, graph, listing, or other form of information.

Figure 7:
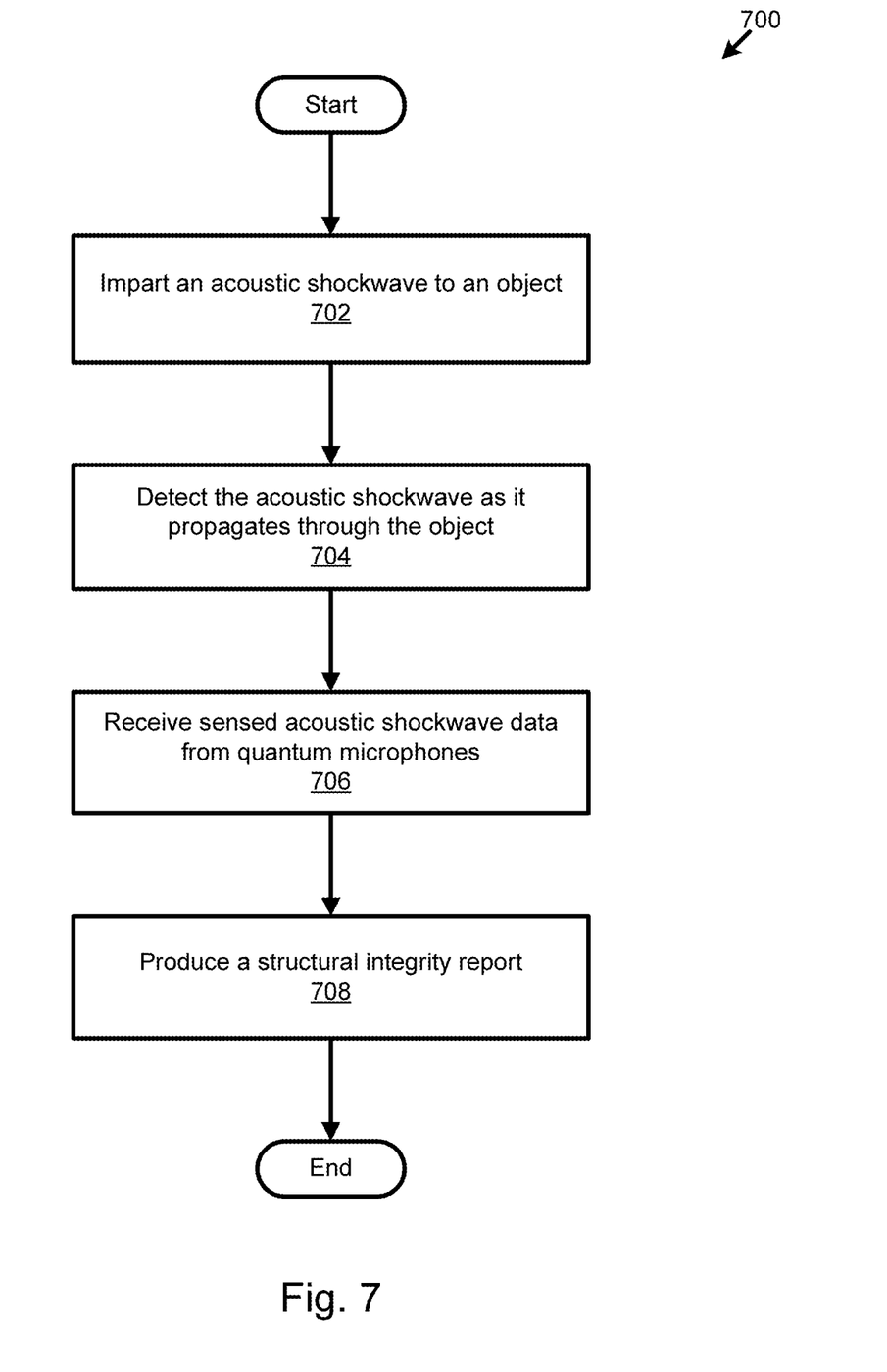
FIG. 7 depicts a method for detecting cracks and structural anomalies, the method including imparting an acoustic shockwave to an object, detecting the acoustic shockwave as it propagates through the object, receiving sensed acoustic shockwave data from quantum microphones, and producing a structural integrity report, according to one embodiment.

FIG. 7 depicts a method 700 for detecting cracks and structural anomalies, wherein the method 700 includes imparting an acoustic shockwave to an object at 702, detecting the acoustic shockwave as it propagates through the object at 704, receiving sensed acoustic shockwave data from quantum microphones at 706, and producing a structural integrity report at 708, according to one embodiment. The acoustic shockwave is imparted to an object 50 at 702 by a vibration initiator 110. The vibration initiator 110 uses an excitation medium 112 to pulse/ping the object, thereby creating a vibration shockwave 114 that ripples outward from the initial interaction point. The acoustic detector array 120 uses quantum microphones 122 to detect the vibration of the object 50 at 704. The sensed shockwave data is received by a reporting unit 130 at 706. The reporting unit 130 produces a structural integrity report at 708 that shows the presence and location of cracks 60 in the object 50.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the subject matter of the present disclosure, however, absent an express correlation to indicate otherwise, an implementation may be associated with one or more embodiments.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive.

What is claimed is:

1. A system for testing a structure of an object having a solid crystal lattice structure, the system comprising:
   a vibration initiator that imparts an acoustic shockwave to an object, the vibration initiator being dedicated for the purpose of imparting the acoustic shockwave to the object, and wherein the vibration initiator is configured to pulse the object and impart an acoustic shockwave such that a phonon of sound is produced by oscillation of atoms in the solid crystal lattice structure of the object;
   an acoustic detector array that senses the phonon of sound generated by the acoustic shockwave as it propagates through the object, wherein the acoustic detector array comprises a plurality of quantum microphones, each of the plurality of quantum microphones being dedicated for the purpose of sensing the phonon of sound, and wherein the vibration initiator is configured differently than each of the plurality of quantum microphones; and
   a reporting unit that receives sensed acoustic shockwave data from the acoustic detector array and produces a structural integrity report.

2. The system of claim 1, wherein the vibration initiator imparts the acoustic shockwave to the object in correlation with the acoustic detector detecting the acoustic shockwave.

3. The system of claim 1, wherein the vibration initiator comprises a laser.

4. The system of claim 1, wherein the vibration initiator comprises a diamond particle pinging subsystem.

5. The system of claim 1, wherein the vibration initiator produces a vibration shockwave in the object that has a frequency greater than 10 MHz.

6. The system of claim 1, wherein the number of quantum microphones on the acoustic detector array is greater than 100.

7. The system of claim 1, wherein the quantum microphones comprise a single-electron transistor.

8. The system of claim 1, wherein the acoustic detector array is bendable.

9. The system of claim 1, wherein the structural integrity report comprises a 2-dimensional image of the structural anomalies of the object.

10. The system of claim 1, wherein the vibration initiator and the acoustic detector array are co-movably fixed together.

11. A controller apparatus, comprising:
   an initiation module that sends an acoustic shockwave command to a vibration initiator to cause the vibration initiator to imparts an acoustic shockwave to an object having a solid crystal lattice structure, the vibration initiator being dedicated for the purpose of imparting the acoustic shockwave to the object, and wherein the vibration initiator is configured to pulse the object and impart an acoustic shockwave such that a phonon of sound is produced by oscillation of atoms in the solid crystal lattice structure of the object;
   a detector module that:
      sends sensing commands to a plurality of quantum microphones on an acoustic detector array, wherein the plurality of quantum microphones are configured to sense the phonon of sound generated by the acoustic shockwave as it propagates through the object, wherein each of the plurality of quantum microphones are dedicated for the purpose of sensing the phonon of sound, and wherein the vibration initiator is configured differently than each of the plurality of quantum microphones,
      receives sensed acoustic shockwave data from the plurality of quantum microphones on the acoustic detector array, and
      produces an acoustic shockwave report based on the sensed acoustic shockwave data; and
   a data module that receives the acoustic shockwave report from the detector module and produces a structural integrity report.

12. The apparatus of claim 11, wherein the initiation module sends a timing correlation command to the detector module, wherein the detector module sends sensing commands to the plurality of quantum microphones on the acoustic detector array according to the timing correlation command.

13. The apparatus of claim 11, wherein the vibration initiator comprises a laser.

14. The apparatus of claim 11, wherein the vibration initiator comprises a diamond particle pinging subsystem.

15. The apparatus of claim 11, wherein the vibration initiator produces a vibration shockwave in the object that has a frequency greater than 10 MHz.

16. The apparatus of claim 11, wherein the quantum microphones comprise single-electron transistors.

17. The apparatus of claim 11, wherein the structural integrity report comprises a 2-dimensional image of the cracks and structural anomalies of an object.

18. A method for testing a structure of an object having a solid crystal lattice structure, the method comprising:
   imparting an acoustic shockwave to the object using a vibration initiator, the vibration initiator being dedicated for the purpose of imparting the acoustic shockwave to the object, wherein imparting the acoustic shockwave comprises pulsing the object and imparting an acoustic shockwave such that a phonon of sound is produced by oscillation of atoms in the solid crystal lattice structure of the object;
   detecting the phonon of sound generated by the acoustic shockwave as it propagates through the object, wherein detecting comprises using a plurality of quantum microphones to sense the acoustic shockwave, each of the plurality of quantum microphones being dedicated for the purpose of sensing the phonon of sound, and wherein the vibration initiator is configured differently than each of the plurality of quantum microphones;
   receiving sensed acoustic shockwave data from the quantum microphones; and
   producing a structural integrity report based on the sensed acoustic shockwave data.

19. The method of claim 18, wherein timing of imparting the acoustic shockwave to the object is correlated with timing of detecting the acoustic shockwave.

20. The method of claim 18, wherein the shockwave imparted to the object has a frequency greater than 10 MHz.

* * * * *

UNITED STATES PATENT AND TRADEMARK OFFICE
CERTIFICATE OF CORRECTION

PATENT NO. : 9,494,561 B1
APPLICATION NO. : 14/024053
DATED : November 15, 2016
INVENTOR(S) : Morteza Safai

Page 1 of 1

It is certified that error appears in the above-identified patent and that said Letters Patent is hereby corrected as shown below:

In the Claims

Column 13, Line 64:
"to imparts an acoustic Shockwave"---should read "to impart an acoustic shockwave"

Signed and Sealed this
Fourteenth Day of February, 2017

Michelle K. Lee
*Director of the United States Patent and Trademark Office*